United States Patent [19]
Maciejewski et al.

[11] Patent Number: 5,415,047
[45] Date of Patent: May 16, 1995

[54] DIFFUSION WELD TEST FIXTURE

[75] Inventors: Wendell C. Maciejewski, Salem; Kurt J. Janecek, Waterford; George J. Kavarnos, New London; Elizabeth A. McLaughlin, Voluntown, all of Conn.

[73] Assignee: The United States of America as represented by the Secretary of the Navy, Washington, D.C.

[21] Appl. No.: 268,341

[22] Filed: Jun. 9, 1994

[51] Int. Cl.⁶ ............................................. G01N 33/20
[52] U.S. Cl. ........................................ 73/850; 73/856
[58] Field of Search ............... 73/841, 842, 843, 844, 73/845, 846, 850, 826, 831, 855, 856

[56] References Cited

U.S. PATENT DOCUMENTS

| | | | |
|---|---|---|---|
| 4,584,881 | 4/1986 | Hogan | 73/842 |
| 4,843,888 | 7/1989 | Gram et al. | 73/856 |
| 4,845,997 | 7/1989 | Radin et al. | 73/831 |
| 5,176,028 | 1/1993 | Humphrey | 73/842 |

Primary Examiner—Richard E. Chilcot, Jr.
Assistant Examiner—Max H. Noori
Attorney, Agent, or Firm—Michael J. McGowan; Prithvi C. Lall; Michael F. Oglo

[57] ABSTRACT

A weld joint test fixture for testing the strength of a weld joining several members forming a test specimen is provided. The fixture includes a base which supports the test specimen and an attachment for applying a testing force to the test specimen while the test specimen is supported by the base. The fixture further includes holding elements attached to the base for holding the test specimen on the base during the application of the testing force. The holding elements preferably engage one of the members forming the test specimen without engaging another of the members. The fixture may also include the holding elements being designed to oppose the testing force substantially only by forces directed in a plane parallel to the applied testing force.

5 Claims, 4 Drawing Sheets

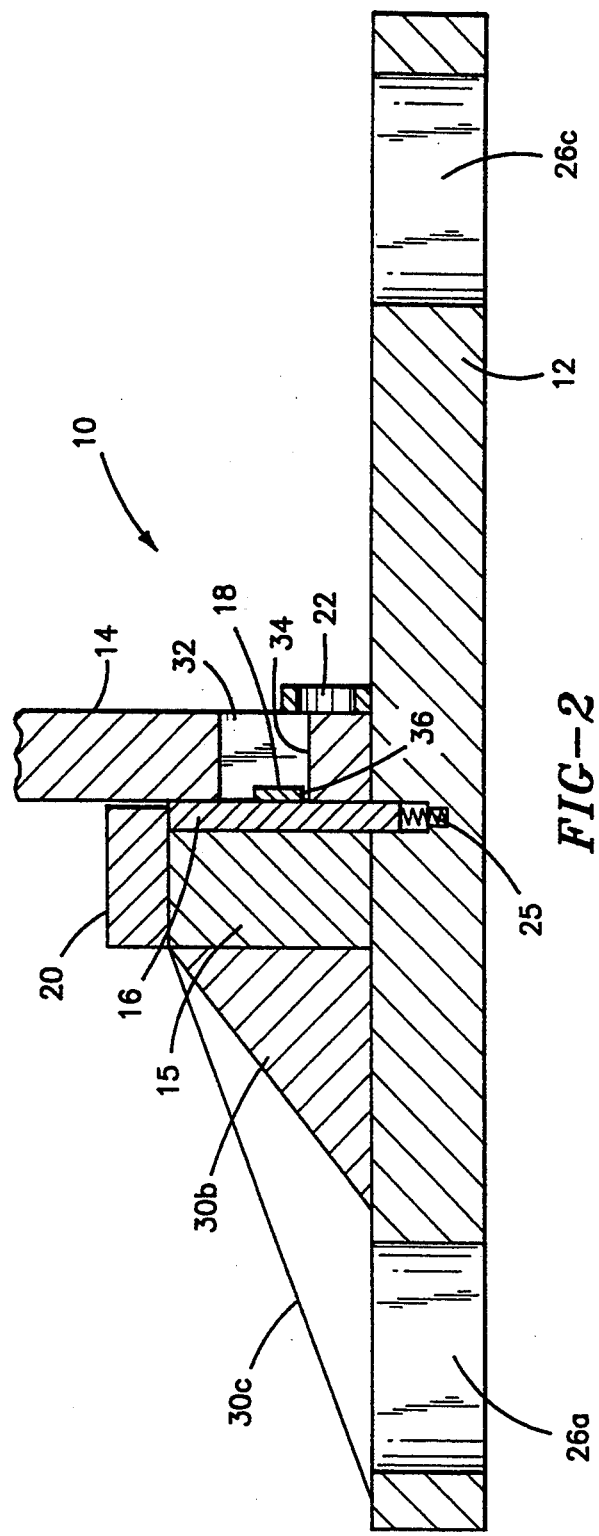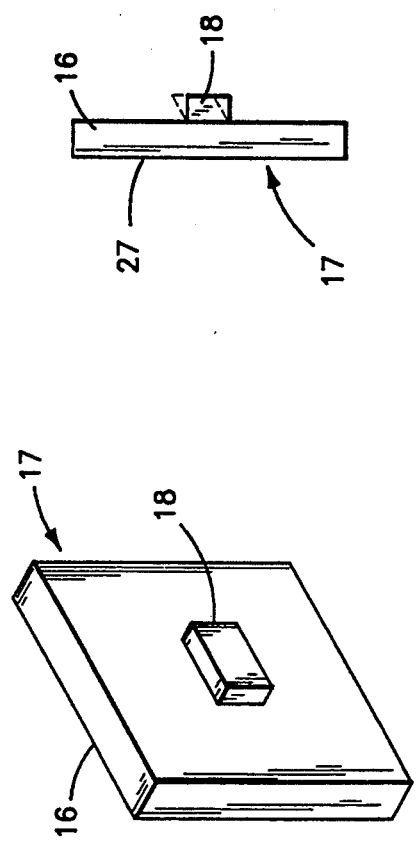

DIFFUSION WELD TEST FIXTURE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

(1) Field of the Invention

This invention is directed toward test fixtures, and more particularly to a test fixture for testing the shear strength of diffusion welds.

(2) Description of the Prior Art

Welding is a well known and commonly used technique for joining metals in configurations for use in supporting structures and the like. Because welding is used to fuse metals which will form a joint that will be subjected to various forces, it is important to know the strength of the weld. It is, of course, possible to calculate shear strengths and bending strengths based on engineering formulas and material properties. However, such formulas usually require a factor of safety so as to account for uncertainties in the material being used, the forces being applied and other unforeseen problems. Because of the uncertainties involved, it is helpful to back up the various formulas and the like with actual physical evidence. Therefore, actual physical testing of the metals or the like for acquiring test data under various circumstances is important in the design process. Therefore, it is desirable to use fixtures or the like to secure the metals and joints in question so that various forces can be applied to the same for determining their actual strength. Such fixtures are particularly important for determining the strength of welded joints, wherein such joints are frequently used for supporting loads in highly critical applications such as bridge trusses, building structures and automobile frames.

The fixture art includes support fixtures for testing the welded joints of articles of manufacture. However, these fixtures, as discussed below, are generally specifically designed for use with the particular articles of manufacture and not for general application to welded joints, as with the inventive fixture disclosed herein.

U.S. Pat. No. 4,012,947 to Tiegel discloses a method and apparatus for testing battery connector welds. In the manufacture of lead storage batteries, battery plates are used within the battery casing in an upstanding orientation. The battery plates must be electrically connected. This is frequently done by welding the plates together through an aperture in the plates. It is important to test the strength of these welds so that the electrical connections are maintained during use of the battery. The Tiegel invention includes the use of anvil and pressure members which bear against opposite edges of the lug projections of the battery. The anvil members engage the battery lug while the pressure member is used for providing a shear force against the immobile lug. The pressure member is forced in a shear direction via a pressure cylinder. If the weld joints successfully resist the shear force applied, the test is deemed successful and the weld joints of sufficient strength. The Tiegel tester is specifically designed for use with battery plate welds and could not easily be used with other test specimens, so that any weld could be tested for shear strength. It is generally unadaptable for use with testing weld joints in general.

U.S. Pat. No. 4,584,881 to Hogan discloses a weld testing head which is also directed for use in testing battery connections. In Hogan, an apparatus is provided which comprises a vertically movable main frame having a recess within a holding surface which is adapted for engagement with the top end of a lug. The lug is restrained from vertical movement. A secondary frame, slidably connected to the main frame, includes two horizontally movable clamping devices which have teeth for engaging the battery lug. The clamping devices are moved against the lug via pressurized cylinders. A vertically oriented pressure cylinder is also used for pulling the secondary frame upward while the clamping devices are engaging the battery lug. A pressure gauge is used to indicate the force being applied, and if the weld joint sustains, under a particular force, the weld joint is considered structurally fit. Similar to Tiegel, the Hogan invention has a particular design directed toward use with battery connector weld joints and lugs. In addition, the Hogan device depends upon the battery weight for providing a base from which to apply the weld testing device. The Hogan testing head engages the test subject via a horizontal clamping force. In using toothed clamps for accomplishing this, the Hogan device risks damage to the specimen being tested.

U.S. Pat. No. 3,566,681 to Iosipescu et al. discloses a shear testing apparatus directed for use with the testing of rocks and other building materials. The apparatus includes a pair of U-shaped calipers which are relatively positioned to form a rectangular enclosure for the insertion of a test specimen. The calipers include pressure members which can be adjusted to apply forces on the specimen in a shear direction. Accordingly, a major feature of the Iosipescu apparatus is the particular shape into which the rock or other building material is to be formed, wherein the particular shape allows for a known shear plane to be created within the specimen. The apparatus is adapted to be placed in an additional testing machine wherein the loads placed on the concrete or other material can be measured. Accordingly, the strength of the material can be determined based on the pressure applied at the point of fracture. The Iosipescu apparatus requires the formation of the specimen into a very unique shape that is obtainable because of the nature of the materials being tested. However, in testing weld joints between metals, it is both inefficient and difficult to shape the testing materials into particular designs simply for testing. Accordingly, the Iosipescu testing fixture is inappropriate for the tests to which the invention disclosed herein is directed.

There exists a need in the materials testing science for the efficient testing of the shear strength of welds between various materials, wherein the test fixture can be used to accurately test weld joint strengths removed from their operative configurations yet without having to arrange the materials in a complex design.

SUMMARY OF THE INVENTION

The primary object of this invention is to provide a weld joint test fixture for determining weld joint strengths from a test specimen.

A further object of this invention is to provide a weld joint test fixture for testing shear strengths of welds, which is adaptable for use with existing testing equipment.

A still further object of this invention is to provide a weld joint test fixture which is specifically designed to hold a test specimen so that only shear forces can be applied to the same, so as to obtain true shear strength readings.

A still further object of this invention is to provide a weld joint test fixture which can be used for testing welded joints between a variety of different materials.

An even further object of this invention is to provide a weld joint test fixture for testing the shear strength of a welded joint, which is not specifically designed for engaging the joint in its operative configuration.

The forgoing objects are attained by the inventive weld joint test fixture for testing the strength of a weld joining several members forming a test specimen of the present invention which broadly includes a base which supports the test specimen; means for applying a testing force to the test specimen while the test specimen is supported by the base; and means attached to the base for holding the test specimen on the base during the application of the testing force. The holding means preferably engages one of the members forming the test specimen without engaging another of the members.

The test fixture may also include means for holding the test specimen on the fixture whereby the testing force is opposed by the holding means substantially only by forces directed in a plane parallel to the applied testing force. In addition, attaching means may also be included for attaching the weld joint test fixture to additional testing equipment used to measure the strength of the weld.

In one embodiment of the invention, the means for applying the testing force may include a load cell adapter which can be connected with a load cell of a testing machine. This embodiment also includes a base formed by a base plate having a single slot therein for engaging a test specimen and several slots for engaging the testing machine. This embodiment may also include means for holding the test specimen formed by a vertically extending mounting bracket, a locking plate, for applying a downward force on the test specimen, and a front brace, which supports the specimen in a transverse direction as well as assisting in guiding the load cell adapter into the fixture for engagement with the test specimen.

Details of the present invention are set out in the following description and drawings wherein like reference characters depict like elements.

BRIEF DESCRIPTION OF THE DRAWINGS

FIG. 2 is a side elevational and cutaway view of the test fixture including a test sample, load cell adapter, and base plate in accordance with the present invention.

FIG. 4 is a perspective view of the test sample including a sample mounting plate.

FIG. 5 is a side view of the test sample and base plate shown in FIG. 4.

DETAILED DESCRIPTION OF THE PREFERRED EMBODIMENT

Figure 1:
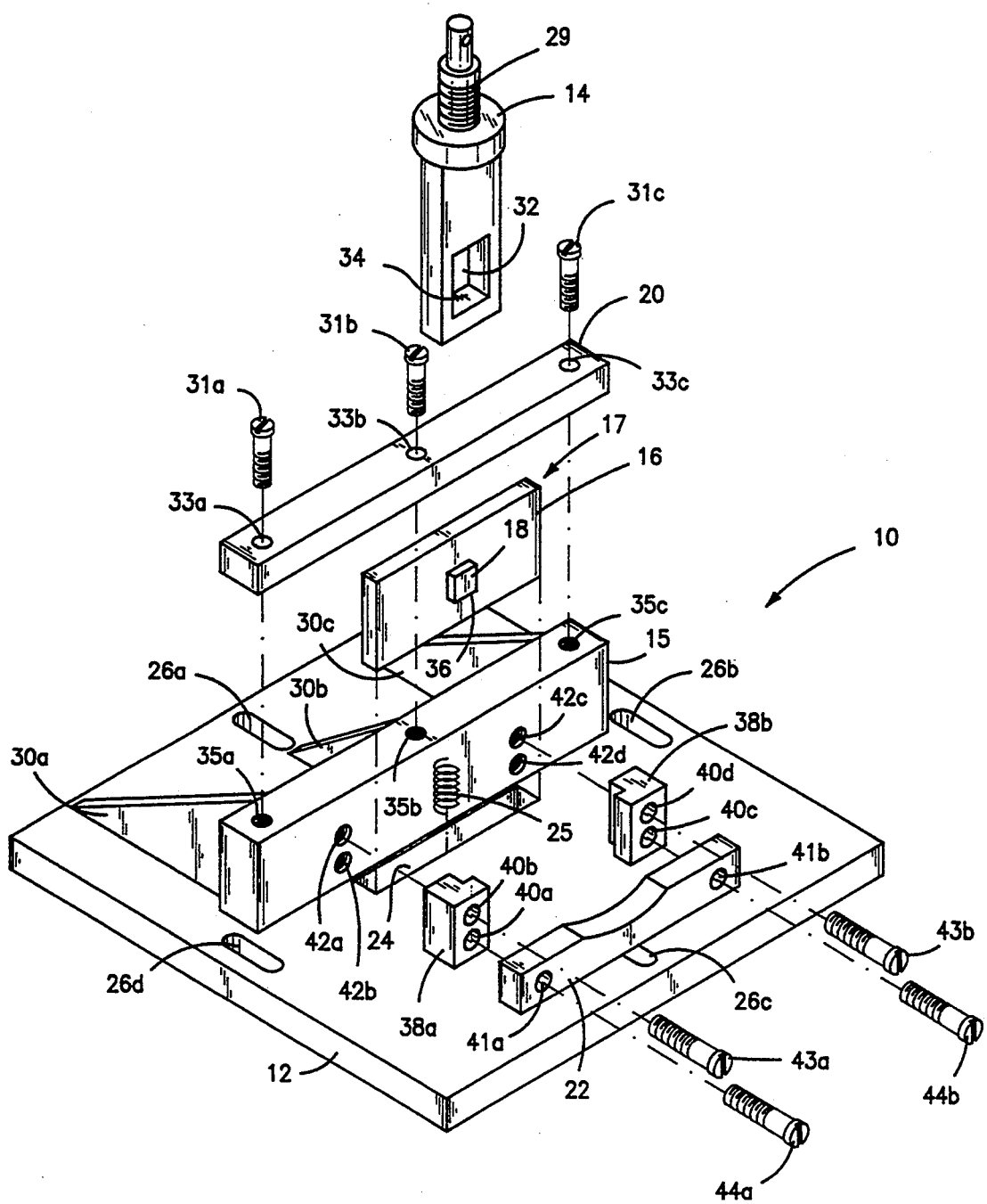
FIG. 1 is an exploded perspective view of the test fixture showing the assembly of the same in accordance with the present invention.

Referring now to the drawings and detail, there is shown in FIG. 1 a perspective exploded view of the weld joint test fixture constructed in accordance with the principles of the present invention and designated generally as 10. As shown in FIG. 1, the test fixture generally includes a base plate 12, a load cell adapter 14, a mounting bracket 15, a test specimen 16 including a sample mounting block 17 having a test sample 18 thereon, a locking plate 20 and a front brace 22.

Figure 3:
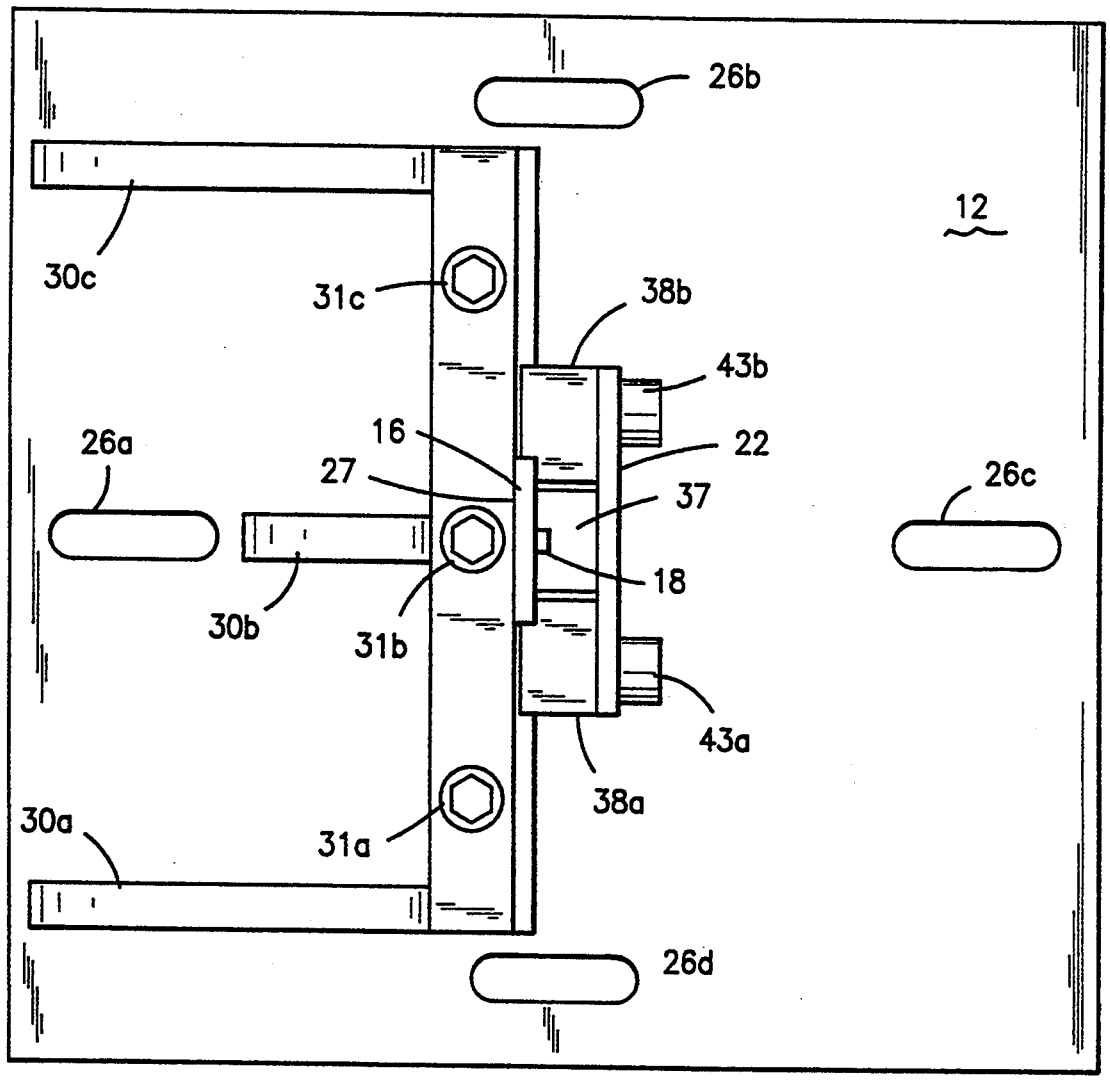
FIG. 3 is an overhead view of the weld joint test fixture as shown in FIG. 2.

Referring to FIGS. 1—3, base plate 12 is preferably comprised of a high strength metal having a substantially rectangular shape, but other suitable shapes or materials may be used. Base plate 12 has a slot 24 machined therein in a substantially horizontal direction for engaging sample mounting block 17 for the purpose of preventing sample movement during loading. Slot 24 is also substantially rectangular in shape and of a size for firmly receiving the width of sample mounting block 17. Slot 24 also has a spring 25 therein for providing an upward force on sample mounting block 17, for pushing sample mounting block 17 against locking plate 20 for further stabilizing test specimen 16. The length of slot 24 should be sufficient to fit the length of sample mounting block 17.

Base plate 12 supports the functional elements of test fixture 10 and has four additional slots 26a–26d which preferably have substantially oval shapes that extend through base plate 12. Slots 26a–26d are substantially equally spaced on base plate 12, as shown in FIG. 3. Slots 26a–26d are used for engaging base plate 12 with a load testing or force actuating machine or the like (not shown). Preferably, slots 26a–26d align with fasteners on the work surface of the load testing machine for bolting base plate 12 to the machine. The elongated nature of slots 26a–26d allows base plate 12 to be adjusted as necessary for proper alignment of load cell adapter 14 with test sample 18.

Mounting bracket 15 is also substantially rectangular in shape having a height which allows it to adjacently contact a vertically extending wall 27 of sample mounting block 17 in its entirety. Mounting bracket 15 extends approximately three quarters of the width of base plate 12 so as to provide sufficient stabilizing support for sample mounting block 17. Mounting bracket 15 is connected to base plate 12 via welding, bolts or other suitable fastening means.

Mounting bracket 15 functions to provide stabilizing support to sample mounting block 17 for preventing bending and horizontal displacement of sample mounting block 17, and supplemental gussets 30a–30c are provided for supporting mounting bracket 15 in the upstanding vertical direction. Gussets 30a–30c are substantially right triangular in shape with the vertical wall of the each gusset extending to a height substantially equal to the height of mounting bracket 15 and abutting the same. Gussets 30a–30c are preferably welded or bolted to base plate 12 and mounting bracket 15, but other means for attachment may be used. Middle gusset 30b is shorter in length than end gussets 30a and 30c so as not to interfere with oval slot 26c and its engagement with the work surface of the additional testing machine.

Referring still to FIGS. 1-3, locking plate 20 functions to maintain a downward force on sample mounting block 17 when an upward testing force is being applied. Accordingly, with sample mounting block 17 engaging slot 24 of base plate 12, the top of sample mounting block 17 is substantially even with the top of mounting bracket 15. Locking plate 20 extends substantially horizontally and adjacent to the top of mounting bracket 15 and sample mounting block 17. As such, locking plate 20 has a depth substantially equal to the combined depth of mounting bracket 15 and sample mounting block 17.

Locking plate 20 has a length substantially equal to the length of mounting bracket 15 and is secured to mounting bracket 15 via three bolts 31a–31c. Bolts 31a–31c extend through clearance holes 33a–33c, respectively, in locking plate 20 and engage threaded holes 35a–35c, respectively, in mounting bracket 15, for securing the same to mounting bracket 15. With locking plate 20 secured to mounting bracket 15, sample mounting block 17 is prevented from moving vertically upon the application of a vertically directed force thereto. That is, sample mounting block 17 is prevented from moving in the vertical direction upon the application of a force via the load testing machine and load cell adapter 14.

Referring still to FIGS. 1–3, front brace 22 is also substantially rectangular in shape and used to abut load cell adapter 14 for maintaining the same adjacent sample mounting block 17, as shown in FIG. 2. Front brace 22 includes two clearance holes therein for the insertion of bolts for securing front brace 22 to mounting bracket 15.

Accordingly, in order to facilitate the securing of front brace 22 adjacent load cell adapter 14 and also to secure sample mounting block 17 against horizontal movement, a pair of L-shaped brackets 38a and 38b are positioned on each side of sample mounting block 17. L-shaped brackets 38a and 38b are positioned so as to engage the outwardly facing vertical edges of sample mounting block 17. That is, the inner corner of the L-shape of brackets 38a and 38b engages the vertical walls and corners of sample mounting block 17, as shown in FIG. 2. L-shaped brackets extend a height sufficient to engage sample mounting block 17 along the entire vertical edge.

L-shaped brackets 38a and 38b extend substantially outward, width wise or horizontally, from the vertical edge of sample mounting block 17. This portion of each L-shaped bracket 38a and 38b extending away from the center of sample 18, is sufficient in size to include clearance holes 40a, 40b, 40c and 40d. Each L-bracket contains two clearance holes. Each of the clearance holes, 40a, 40b, 40c and 40d are located such that they align themselves with threaded holes 42a, 42b, 42c and 42d in the mounting bracket 15. Bolts 43a and 43b are then used in the upper holes 40b and 40d of the L-brackets 38a and 38b to secure the bracket to the mounting block 15. Bolts 44a and 44b are inserted through the clearance holes 41a and 41b of front brace 22 and holes 40a and 40b of the L-brackets into holes 42b and 42d of the mounting bracket. These bolts are tightened sufficiently enough to secure the front brace 22, and the L-brackets 38a and 38b to the mounting bracket 15 thereby firmly holding the test specimen 16.

Test specimen 16 including sample mounting block 17 and test sample 18 are prepared as shown in FIGS. 4 and 5, prior to use in test fixture 10. Sample mounting block 17 is substantially rectangular in shape having a width that fits within slot 24 of base plate 12. As discussed, the height of sample mounting block 17 is such that as it engages slot 24 and is pushed upwardly by spring 25, the top edge of sample mounting block 17 is substantially even with the top edge of mounting bracket 15. As shown in FIG. 4, test sample 18 is to be welded to sample mounting block 17 by way of diffusion welding. Test sample 18 and sample mounting block 17 are representative of the materials in which the weld joint will be used to join.

Test sample 18 is preferably welded near the center of sample mounting block 17 for engaging load cell adapter 14, as discussed below. The width of test sample 18 is sufficient for allowing secure engagement by load cell adapter 14, as shown in FIG. 2. As discussed above, sample mounting block 17 and test sample 18 are maintained in a substantially vertical orientation via the application and arrangement of the plurality of blocks, brackets and gussets. It is important, that the dimension tolerances and machining of the elements forming the test fixture 10 including the slots and the like are accurate so that a vertical orientation of mounting bracket 15 is substantially maintained by the fixture structure. With a vertical orientation maintained, a true shear load can be applied to test sample 18. However, if the tolerances and machining are not accurate, an angular load would be applied to the test sample 18 potentially causing compression and torsional forces instead of a direct vertical shear force. As such, proper readings on the shear strength of the weld would not be obtainable.

Figure 6:
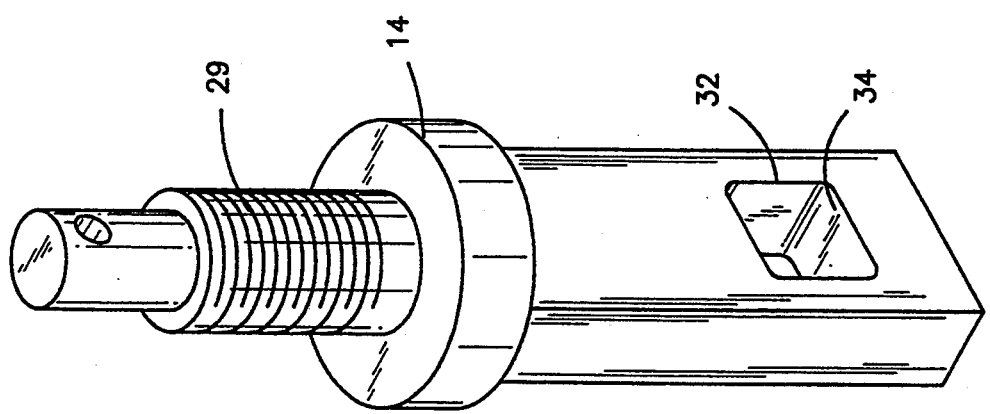
FIG. 6 is a perspective view of the load cell adapter.

Load cell adapter 14 shown perspectively in FIG. 6, is preferably formed from a metal bar or the like and is preferably rectangular in shape. As shown in FIG. 6 and in FIG. 1, the top end of load cell adapter 14 has a connector means, for example, a cylindrical male upper extension 29 with a crosshole forming its upper end, for attaching the same to the force actuating testing machine, shown partially in FIG. 7, such as, for example, a suitable tension/compression test machine, which can provide a load in the vertical direction while measuring the capacity of test sample 18 to resist the same. There is a threaded portion 29a below the cylindrical male end which will accept a jam-nut that could be tightened against the load cell connector if required. This invention contemplates the use of a variety of ends whereby load cell adapter 14 could be attached to a variety of machines.

Load cell adapter 14 is substantially rectangular in shape immediately below cylindrical male upper extension 29. Adjacent to the bottom end, however, there is a rectangular opening or cutout 32, as shown in FIG. 6 and in FIG. 1, which is adapted to engage test sample 18, as shown in FIG. 2. Rectangular cutout 32 preferably has rounded corners and is centered widthwise on the load cell adapter 14. All edges are to be square and sharp to achieve a full contact engagement with the edges of test sample 18. Rectangular cutout 32 also extends entirely through the depth of load cell adapter 14. In order to obtain accurate shear strength readings, it is pertinent that rectangular cutout 32 is of a size which entirely fits test sample 18 therein. That is, the corners of test sample 18 cannot engage the rounded corners of rectangular cutout 32 because such contact could cause torsional forces to act on test sample 18, and effect the test as discussed above. A lower edge 34 of rectangular cutout 32 is adapted to engage a lower lip 36 of test sample 18 upon the application of the test force to the upper portion of load cell adapter 14. As shown in FIG. 1, load cell adapter 14 extends substantially vertically and is sized to fit within cavity 37 formed by the combination of sample mounting block 17, locking plate 20, front brace 22 and L-shaped brackets 38a and 38b. Accordingly, load cell adapter 14 is guided between sample mounting block 17 and front brace 22.

With the above construction and arrangement of brackets and braces and blocks, a rectangular cavity 37 is formed for the insertion of load cell adapter 14, wherein the back and front walls are formed by sample mounting block 17 and front brace 22, respectively, and the side walls are formed by L-shaped brackets 38a and 38b. The size of cavity 37 is such that a close tolerance sliding fit is formed between load cell adapter 14 and cavity 37. Accordingly, load cell adapter 14 is confined to substantially vertical movement by cavity 37 upon the application of a load from the test instrument and test sample 18 is restricted to primarily vertical displacement. The fixture structure opposes the load primarily along a plane parallel to the load, thus restricting the mounting block 17 from movement without damaging test sample 18 and potentially effecting the accuracy of the test results.

Test fixture 10 can be used as described below. To begin, test sample 18 is welded to sample mounting block 17 in the orientation as discussed above. Referring to the exploded view shown in FIG. 1, sample mounting block 17 is inserted into slot 24 of base plate 12, adjacent mounting bracket 15, previously fastened to base plate 12. Locking plate 20 is then installed and secured to mounting bracket 15 via bolts 31a–31c for holding the test specimen 16 down. L-shaped brackets 38a and 38b are then positioned on each side of sample mounting block 17 so as to engage the vertically extending edges of the same. As such, sample mounting block 17 is firmly held so as to be secured from both vertical and horizontal movement.

Base plate 12, with substantially the entire fixture assembled, can now be placed onto test fixture 10. Slots 26a–26d are aligned with the fasteners or the like connected with the work surface of the test instrument. Once base plate 12 is aligned therewith, bolts or the like are used to first loosely secure base plate 12 to the work surface of the test machine. Load cell adapter 14 is then attached to the test device, such as a tension/compression machine, and moved into place adjacent test sample 18. Illustrative of such a tension/compression machine is a Model 4206 Instrom tester manufactured by Instrom Corporation of Canton, Mass. Rectangular cutout 32 of load cell adapter 14 is maneuvered, from the front of fixture 10, between L-shaped brackets 38a and 38b and around test sample 18, as shown in FIG. 2, so that lower edge 34 is adjacent lower lip 36 of test sample 18.

Once in place, base plate 12 is adjusted so that load cell adapter 14 is parallel and in adjacent contact with sample mounting block 17. The surface contact between load cell adapter 14 and any other surface (except the sample 18) should be minimized to avoid friction problems. L-shaped brackets 38a and 38b and front brace 22 are firmly secured via bolts 43a, 43b, 44a and 44b as shown in FIG. 1, through clearance holes 40a–40d in the L-shaped brackets and into threaded holes 42a–42d in mounting bracket 15. At this juncture, all of the elements of test fixture 10 are substantially in place and the last step for the installation of fixture 10, is simply to tighten all of the loose bolts while maintaining the vertical and parallel orientations between mounting bracket 15, sample mounting block 17 and load cell adapter 14.

Figure 7:
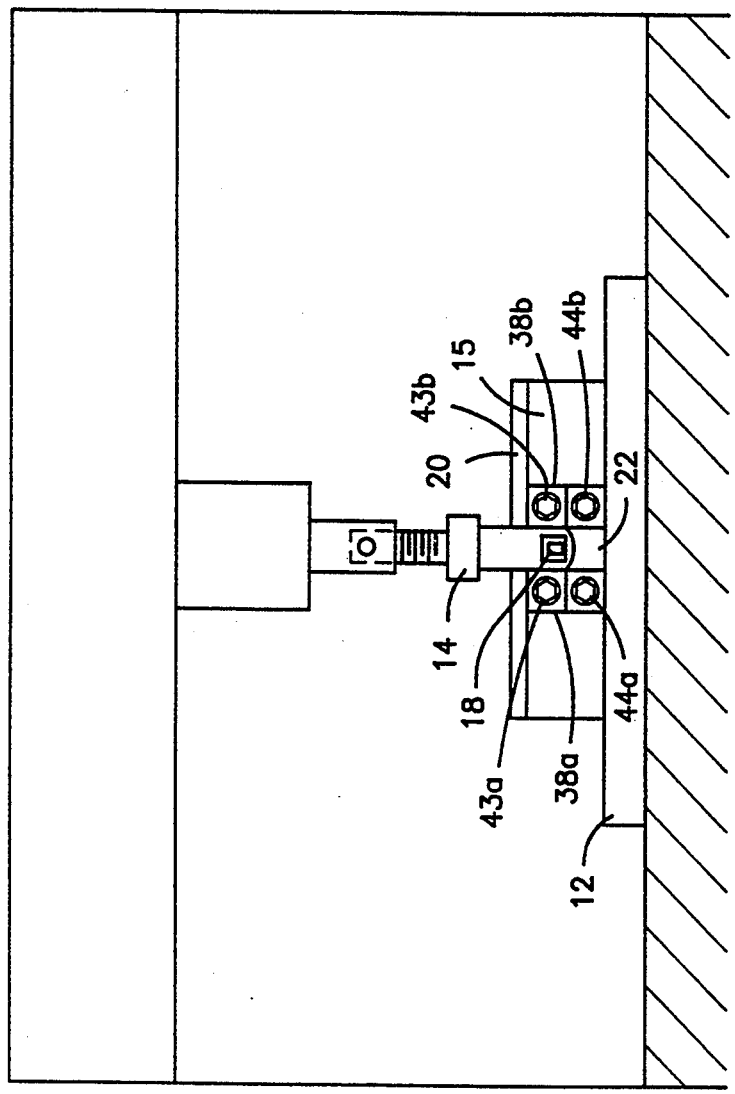
FIG. 7 is a front elevational view showing the test fixture connected with a force actuating machine.

The strength of the weld joint is then tested by applying a load via the test machine to load cell adapter 14 and pulling vertically upward on test sample 18, as shown in FIG. 7. By using the measuring capabilities of the test machine, the shear strength of the weld can be determined by incrementally increasing the load applied to test sample 18 and measuring the displacement of the same. Preferably, load cell adapter 14 is raised at some prescribed rate and the load and displacement of test sample 18 is recorded. These recorded values can be used to establish a stress strain relationship of the welded joint.

The primary advantage of this invention is that it provides a weld joint test fixture for testing weld joint strengths using a test specimen. Another advantage of this invention is that it provides a weld joint test fixture for testing shear strengths of welds wherein the fixture can be used with existing force actuating and testing equipment. An additional advantage of this invention is that a weld joint test fixture is provided which is specifically designed to hold the test specimen so that only a shear force can be applied to the specimen, so that only a true shear strength reading is obtained. Another advantage of this invention is that a weld joint test fixture is provided which can be used for testing weld joints between any metals. An additional advantage of this invention is that a weld joint test fixture is provided for testing the shear strength of the weld joint without having to have the weld joint in its operative configuration.

It is apparent that there has been provided in accordance with this invention a weld joint test fixture which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A weld joint test fixture for testing the strength of a weld joining a first and a second member, which first and second members together form a test specimen, said fixture comprising:
   a base which supports said test specimen;
   means for attaching said test fixture to a force actuating mechanism;
   means for applying a testing force to said test specimen while said test specimen is supported by said base; and
   means attached to said base for holding said test specimen on said base during the application of said testing force, wherein said holding means engages said first member of said test specimen, said base comprising a plate and said attaching means comprising slots in said plate which are adapted to engage said force actuating mechanism.

2. A weld joint test fixture for testing the strength of a weld joining a first and a second member, which first and second members together form a test specimen, said fixture comprising:
   a base which supports said test specimen;
   means for applying a testing force to said test specimen while said test specimen is supported by said base;

means attached to said base for holding said test specimen on said base during the application of said testing force, wherein said holding means engages said first member of said test specimen; and said base having a slot therein for engaging said first member of said test specimen.

3. A weld joint test fixture for testing the strength of a weld joining a first and a second member, which first and second members together form a test specimen, said fixture comprising:

a base which supports said test specimen;

means for applying a testing force to said test specimen while said test specimen is supported by said base, said applying means comprising a bar and said engaging means comprising an opening in said bar, said opening being shaped to fit around said second member comprising said test specimen for engaging said second member when said testing force is applied, said applying means including means for receiving said second member comprising said test specimen; and means attached to said base for holding said test specimen on said base during the application of said testing force, said holding means engaging said first member of said test specimen.

4. A weld joint test fixture for testing the strength of a weld joining a first and a second member, which first and second members together form a test specimen, said fixture comprising:

a base which supports said test specimen;

means for applying a testing force to said test specimen while said test specimen is supported by said base; and means attached to said base for holding said test specimen on said base during the application of said testing force, where said holding means engages said first member of said test specimen, said holding means comprising a plurality of plates and brackets arranged on said base to interact with said applying means, and said plates and brackets form a cavity which confines said first member of said test specimen in a manner so as to prevent said test specimen from moving in a direction substantially transverse to the direction of said testing force.

5. The weld joint test fixture according to claim 4, wherein said plurality of plates and brackets includes:

a substantially vertically oriented mounting bracket connected to said base and adapted to be adjacent said test specimen for rearward stabilization of said test specimen;

a pair of brackets positioned adjacent said test specimen and opposite said mounting bracket for frontward stabilization of said test specimen;

a locking plate extending adjacently above and over said mounting bracket and said test specimen for holding said test specimen downward against said testing force; and a front brace positioned adjacent said brackets and adapted to be positioned adjacent said applying means for maintaining said applying means adjacent said test specimen;

wherein said mounting bracket, said pair of brackets, said locking plate and said front brace form said cavity in which said test specimen and said applying means are prevented from movement substantially traverse to said direction of said testing force.

* * * * *